(12) United States Patent
Huang et al.

(10) Patent No.: US 12,313,636 B2
(45) Date of Patent: *May 27, 2025

(54) SERUM METABOLIC BIOMARKERS FOR DETECTING TUBERCULOSIS AND TUBERCULOSIS DETECTION KIT

(71) Applicant: Zhejiang SUKEAN Pharmaceutical Co., Ltd., Hangzhou (CN)

(72) Inventors: Pintong Huang, Hangzhou (CN); Yajing Liu, Hangzhou (CN); Yan Su, Hangzhou (CN); Chao Zhang, Hangzhou (CN)

(73) Assignee: Zhejiang SUKEAN Pharmaceutical Co., Ltd., Hangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/350,764

(22) Filed: Jul. 12, 2023

(65) Prior Publication Data

US 2023/0358766 A1 Nov. 9, 2023

Related U.S. Application Data

(63) Continuation of application No. PCT/CN2022/136421, filed on Dec. 5, 2022.

(30) Foreign Application Priority Data

Mar. 29, 2022 (CN) .......................... 202210321998.X

(51) Int. Cl.
  *G01N 33/68* (2006.01)
  *G01N 33/53* (2006.01)
  *G01N 33/569* (2006.01)
  *G01N 33/92* (2006.01)

(52) U.S. Cl.
  CPC ..... *G01N 33/6893* (2013.01); *G01N 33/5308* (2013.01); *G01N 33/5695* (2013.01); *G01N 33/92* (2013.01); *G01N 2800/26* (2013.01)

(58) Field of Classification Search
  None
  See application file for complete search history.

(56) References Cited

U.S. PATENT DOCUMENTS

| 9,046,538 B2 * | 6/2015 | Laaksonen | G01N 33/92 |
| 2010/0233724 A1 * | 9/2010 | Watkins | G01N 33/92 |
| | | | 435/7.1 |
| 2012/0286157 A1 * | 11/2012 | Fuhrmann | G01N 33/92 |
| | | | 250/282 |
| 2016/0298165 A1 * | 10/2016 | Hartman | A61K 31/4409 |
| 2018/0067138 A1 * | 3/2018 | Laaksonen | A61P 9/10 |

FOREIGN PATENT DOCUMENTS

WO WO-2018007422 A1 * 1/2018

* cited by examiner

*Primary Examiner* — Changhwa J Cheu
(74) *Attorney, Agent, or Firm* — Andrew C. Cheng

(57) ABSTRACT

A set of serum metabolic biomarkers and detection kit for detecting tuberculosis are provided. The set of the serum metabolic biomarkers includes 17 serum metabolic biomarkers. The 17 serum metabolic biomarkers comprising D-Leucic acid, Leucinic acid, L-Cystine, MG(0:0/14:0/0:0), S-Lactoylglutathione, Octacosanoic acid, Cer(d18:1/12:0), Raffinose, LysoPC(20:1(11Z)/0:0), LysoPC(22:4(7Z,10Z, 13Z,16Z)/0:0), PC(18:1(9Z)e/2:0), Torvoside G(TG(15:0/ 15:0/15:0)), CE(16:1(9Z)), all-trans-Heptaprenyl diphosphate, PC(15:0/16:0), NADP, TG(20:0/20:0/20:1(11Z)). The 17 serum metabolic biomarkers are verified to be associated with tuberculosis based on the level changes of these biomarkers. The tuberculosis detection model based on the levels of the 17 metabolic biomarkers can achieve an area under the ROC curve of 99.5%, sensitivity of 98.2%, and specificity of 95.8% in detecting tuberculosis. The serum metabolic biomarkers and detection kit for detecting tuberculosis can assist doctors in accurately diagnosing the disease, which is of great significance for the diagnosis and mass screening for tuberculosis.

1 Claim, 1 Drawing Sheet

SERUM METABOLIC BIOMARKERS FOR DETECTING TUBERCULOSIS AND TUBERCULOSIS DETECTION KIT

CROSS REFERENCE TO RELATED APPLICATION

This application is a Continuation of PCT Patent Application No. PCT/CN2022/136421 filed on Dec. 5, 2022, which claims priority of China Patent Application No. 202210321998.X, filed on Mar. 29, 2022. The contents of the above-identified applications are incorporated herein by reference.

TECHNICAL FIELD

The disclosure relates to the field of biology technology, and in particular to serum metabolic biomarkers for detecting tuberculosis and a tuberculosis detection kit.

BACKGROUND

The gold standard for tuberculosis detection is pathogen detection, which involves the identification of large quantities of live bacteria. This method is time-consuming, requires a high level of technical proficiency, and necessitates strict laboratory biosafety measures. Consequently, its application is limited in economically underdeveloped areas, hindering early tuberculosis control efforts. In recent years, molecular biological detection technologies such as polymerase chain reaction (PCR), DNA probe technology, DNA sequence determination, and gene chip technology have been developed. However, these methods have limitations due to their demanding operational requirements and high costs. As a result, there is a significant demand for rapid and accurate point-of-care diagnostic tests, which would greatly aid in infection control, reducing transmission opportunities, and suppressing the tuberculosis epidemic.

The metabolome is at the very downstream of systems biology, where subtle functional changes in the genome and proteome can be amplified at the metabolic level. Analyzing metabolites in biological fluids provides a more direct and accurate reflection of an organism's pathophysiological state. Metabolomics, a high-throughput approach for detecting metabolites in the body, combined with multivariate statistical analysis, can identify metabolic biomarkers that exhibit significant differences. By identifying changes in an organism's metabolites, metabolic biomarkers shed light on disease diagnostics, disease progression, and drug resistance mechanisms. Tuberculosis induces systemic changes not only at the site of infection but also in the overall body metabolism. Consequently, the use of metabolomic methods to search for tuberculosis diagnostic biomarkers holds great clinical value.

SUMMARY

The present disclosure introduces a serum metabolic biomarker panel and a tuberculosis detection kit for the accurate detection of tuberculosis. The serum metabolic biomarkers effectively address the limitations of current tuberculosis detection methods, leading to improved detection accuracy.

In the first aspect of the disclosure, the serum metabolic biomarkers for tuberculosis detection comprise 17 metabolites present in the serum of patients with tuberculosis. These metabolites include D-Leucic acid, Leucinic acid, L-Cystine, MG(0:0/14:0/0:0), S-Lactoylglutathione, Octacosanoic acid, Cer(d18:1/12:0), Raffinose, LysoPC(20:1(11Z)/0:0), LysoPC(22:4(7Z,10Z,13Z,16Z)/0:0), PC(18:1(9Z)e/2:0), Torvoside G(TG(15:0/15:0/15:0)), CE(16:1(9Z)), all-trans-Heptaprenyl diphosphate, PC(15:0/16:0), NADP, and TG(20:0/20:0/20:1(11Z)).

These metabolic biomarkers exhibit high sensitivity and specificity for tuberculosis detection, making them crucial for effective tuberculosis treatment.

The present disclosure also provides a screening method for detecting tuberculosis by analyzing serum metabolic biomarkers. The screening method consists of the following steps: 1. Collection of 1-2 mL of blood from both tuberculosis (TB) patients and healthy individuals who are in a fasting state, using a venous blood collection tube (BD, 367955 SST II). 2. Centrifugation of the collected blood at 4° C. and 3500 rpm for 10 minutes, within two hours of collection. 3. Separation of the upper serum (0.3 mL to 1.5 mL) from the centrifuged blood into a new EP tube, followed by storage at −80° C. 4. Preparation for the LDI MS experiment, which involves dispersing iron particles in water at a concentration of 1 mg/mL as a substrate, diluting the upper serum 10 times with water, placing 1 μL of the diluted serum on a polishing plate, and adding 1 μL of the substrate to the diluted serum. 5. Analysis of each serum sample using the LDI MS technique, and recording the original metabolic fingerprints on an AutoFlex TOF/TOF mass spectrometer (Bruker, Germany). 6. Pre-processing of the original metabolic fingerprints using MATLAB (R2016a, the MathWorks, USA) to make them suitable for statistical analysis. This pre-processing includes baseline correction, peak detection, extraction, comparison, normalization, and standardization. 7. Training the data by randomly selecting 3/4 of the data as the training set and using 1/4 as the testing set. This is done using the Partial Least Squares (PLS) algorithm. 8. Establishment of a detection model and creation of a receiver operating characteristic (ROC) curve for the data using the Random Forest (RF) algorithm. 9. Performance of variance analysis and enrichment analysis of the data using MetaboAnalyst 5.0 software. 10. Selection of differential data based on the detection model. The selected data must meet the following criteria: a frequency greater than 90%, a p-value less than 0.05, and a VIP value greater than 1. These selected differential data are then compared with spectrogram information in the human Metabolome database (HMDB) to identify the metabolites that serve as the 17 serum metabolic biomarkers for tuberculosis detection.

A tuberculosis detection model utilizing the Partial Least Squares (PLS) algorithm in machine learning is established based on 17 carefully selected serum metabolic biomarkers. The aforementioned steps are followed to process the blood samples of patients undergoing testing in order to obtain the necessary data. Subsequently, the data is input into the tuberculosis detection model to identify the presence of tuberculosis in the patients. Another aspect of this disclosure pertains to a tuberculosis detection kit that incorporates the measurement of the 17 metabolic biomarkers in the serum of tuberculosis patients. This detection kit enables the quantitative assessment of the aforementioned biomarkers in the serum of individuals suspected of having tuberculosis. The 17 metabolites encompass D-Leucic acid, Leucinic acid, L-Cystine, MG(0:0/14:0/0:0), S-Lactoylglutathione, Octacosanoic acid, Cer(d18:1/12:0), Raffinose, LysoPC(20:1(11Z)/0:0), LysoPC(22:4(7Z,10Z,13Z,16Z)/0:0), PC(18:1(9Z)e/2:0), Torvoside G(TG(15:0/15:0/15:0)), CE(16:1

(9Z)), all-trans-Heptaprenyl diphosphate, PC(15:0/16:0), NADP, and TG(20:0/20:0/20:1(11Z)).

For the first time, the disclosure has discovered an association between the aforementioned 17 metabolic biomarkers and pulmonary tuberculosis. Through metabolomics analysis, it is observed that the levels of these 17 metabolites in the serum of tuberculosis patients deviate from the norm. By integrating these 17 serum metabolic biomarkers with metabolomics analysis and machine learning, a highly effective tuberculosis detection model is established, which is subsequently evaluated using the ROC curve. The tuberculosis detection model, based on the levels of these 17 metabolic biomarkers, exhibits an outstanding performance with an area under the ROC curve of 99.5% for tuberculosis detection, demonstrating a sensitivity of 98.2% and a specificity of 95.8%.

This disclosure harnesses the potential of serum metabolomics technology and machine learning methods to identify suitable biomarkers and construct a robust detection model for tuberculosis. The developed tuberculosis detection model offers exceptional effectiveness, characterized by high sensitivity and commendable specificity, rendering it suitable for tuberculosis detection. Furthermore, this disclosure enables tuberculosis diagnosis through a straightforward blood test, which is not only rapid but also requires a small sample size of only 50 nL, thus facilitating mass screening for tuberculosis and holding significant clinical value.

DETAILED DESCRIPTION OF THE EMBODIMENTS

The embodiments presented in this disclosure serve solely to elucidate the invention and do not imply any limitation on the scope of protection provided by the disclosure.

In Step 1, the study enrolls the research subjects.

Between 2020 and 2021, a total of 228 participants were recruited from Hangzhou Red Cross Hospital and the Second Affiliated Hospital of Zhejiang University. The sample includes 110 individuals diagnosed with pulmonary tuberculosis (TB) and 118 healthy individuals. The diagnosis of pulmonary TB was based on the following criteria: (A) positive sputum smear, (B) positive MTB cultures, (C) positive nucleic acid detection for MTB, (D) chest radiograph (X-ray or CT scan), and (E) pulmonary histopathology diagnosis of TB.

In Step 2, the blood samples undergo pre-treatment.

1-2 mL of venous blood (to prevent lipolysis and hemolysis) is collected and injected into a vacuum blood collection tube. The tube is immediately inverted 5-8 times to ensure thorough mixing of the coagulant adhering to the tube wall with the blood. Subsequently, the tube is kept at room temperature (20° C.-25° C.) for approximately 30 minutes to allow complete clotting of the blood. Once the serum has fully separated, it is centrifuged at 3500 rpm for 10 minutes. Careful aspiration of approximately 0.3-1.5 mL of the clear liquid from the top layer is performed, and the obtained serum is transferred into a tightly sealed centrifuge tube. The tube's seal is checked, and the centrifuge tube is placed in a sample box and stored at −80° C.

In Step 3, machine detection is performed.

Figure 1:
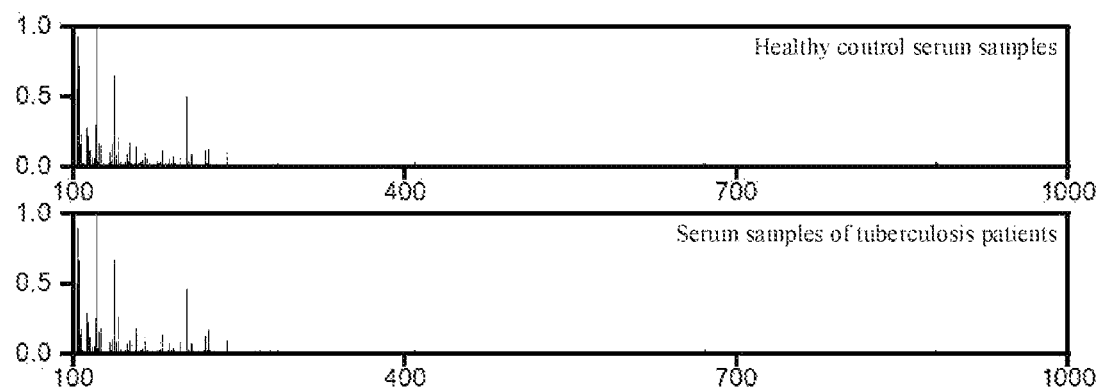
FIG. 1 illustrates typical mass spectra from a healthy control and a TB patient.

The iron particle-assisted laser desorption/ionization mass spectrometry (LDI-MS) technique is employed, utilizing iron particles dispersed in water at a concentration of 1 mg/mL as the matrix. The diluted serum (1 μL) is directly spotted onto a polished plate, air-dried at room temperature, and subsequently mixed with 1 μL of the matrix solution prior to LDI-MS analysis. Mass spectra are acquired using an AutoFlex TOF/TOF mass spectrometer (Bruker, Germany) equipped with a Nd:YAG laser (2 kHz, 355 nm). The acquisition is conducted in a positive reflection ion mode with delayed extraction. The repetition frequency is set at 1000 Hz, and the acceleration voltage is maintained at 20 kV. The delay time is optimized at 250 ns for all LDI-MS experiments. Each analysis involves 2000 laser shots. Following the acquisition of the raw mass spectrometry data (as depicted in FIG. 1), MATLAB code (R2016a, The MathWorks, USA) is employed for peak picking, alignment, normalization, and standardization preprocessing, thus transforming the raw data into a suitable format for subsequent analysis.

In Step 4, disease models are constructed based on machine learning.

A detection model is established utilizing the partial least squares (PLS) algorithm. For learning purposes, 3/4 of the tuberculosis and healthy serum sample data are randomly selected as the training set, while the remaining 1/4 is allocated as the test set. By employing this training set, the disease model is developed. Subsequently, a receiver operating characteristic (ROC) curve is plotted, and the area under the curve (AUC) of the model is calculated to be 94.5%.

In Step 5, metabolites are screened.

Differential metabolites are identified based on specific criteria. Metabolites with a VIP value greater than 1, model selection frequency exceeding 90%, and a p-value lower than 0.05 are selected as the differential metabolites. These include 17 metabolites, as presented in Table 1.

In Step 6, a tuberculosis detection model is established utilizing the partial least squares (PLS) algorithm. The model is developed based on the 17 identified differential metabolites, and a receiver operating characteristic (ROC) curve is plotted to evaluate its performance.

Figure 2:
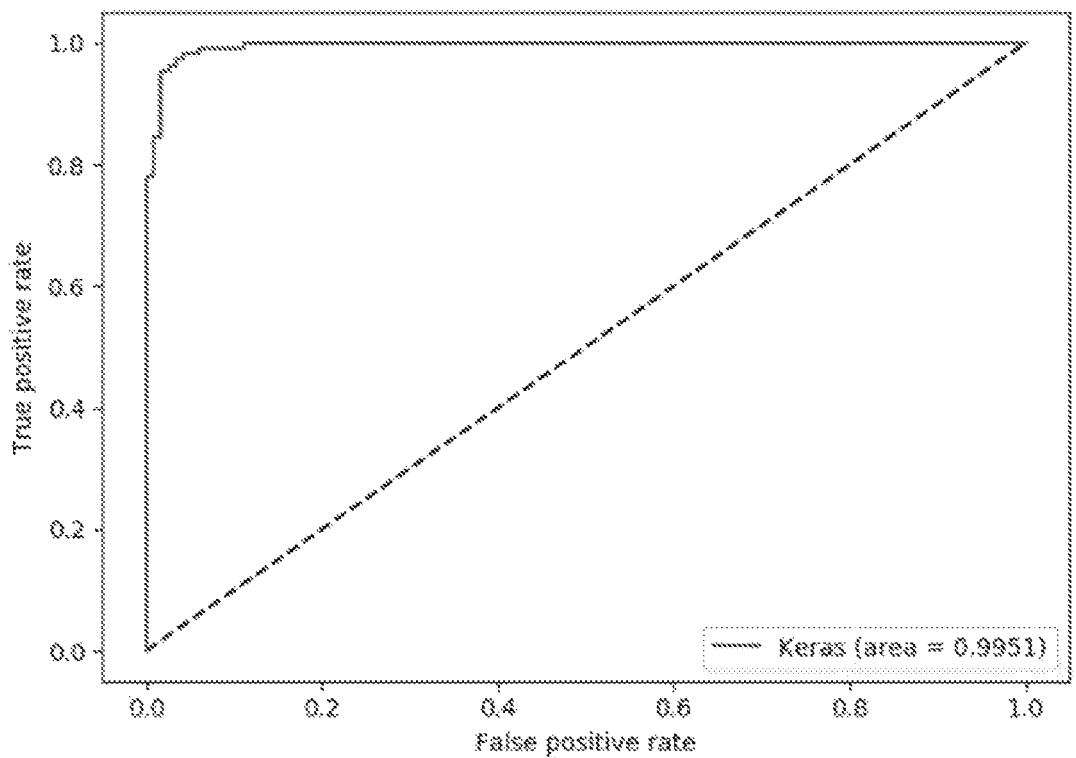
FIG. 2 illustrates a classification performance of a tuberculosis detection model constructed using 17 serum metabolic biomarkers.

The classification performance of the tuberculosis detection model is illustrated in FIG. 2, demonstrating an area under the curve (AUC) of 99.5%, sensitivity of 98.2%, and specificity of 95.8%. In conclusion, the accuracy and specificity of tuberculosis detection utilizing the 17 serum metabolic markers are deemed satisfactory. The tuberculosis detection process involves the utilization of the tuberculosis detection model, encompassing the following steps.

The blood samples are processed following the methodology described in Step 2 above. Subsequently, raw metabolic fingerprints are acquired using the procedure outlined in Step 3. The data obtained from the previous step is then input into the model established using the 17 serum metabolic markers in Step 6. By analyzing the model output, it becomes feasible to determine whether an individual's blood sample tests positive for tuberculosis. The tuberculosis detection is conducted using the tuberculosis detection kit, employing the subsequent steps.

The blood sample undergoes pretreatment as described in Step 2. Subsequently, the tuberculosis detection kit is utilized to assess the levels of the 17 serum metabolic biomarkers mentioned earlier. The analysis of these biomarkers' levels aids in determining the presence of tuberculosis.

TABLE 1

| | m/z | Name of potential substance | HMDB ID |
|---|---|---|---|
| 1 | 155.102 | D-Leucic acid | HMDB0000624 |
| 2 | 155.102 | Leucinic acid | HMDB0000665 |
| 3 | 279.033 | L-Cystine | HMDB0000192 |
| 4 | 303.288 | MG(0:0/14:0/0:0) | HMDB0011530 |
| 5 | 380.147 | S-Lactoylglutathione | HMDB0001066 |
| 6 | 425.418 | Octacosanoic acid | HMDB0002348 |
| 7 | 504.483 | Cer(d18:1/12:0) | HMDB0004947 |
| 8 | 527.117 | Raffinose | HMDB0003213 |
| 9 | 572.388 | LysoPC(20:1(11Z)/0:0) | HMDB0010391 |
| 10 | 572.388 | LysoPC(22:4(7Z, 10Z, 13Z, 16Z)/0:0) | HMDB0010401 |
| 11 | 572.388 | PC(18:1(9Z)e/2:0) | HMDB0011148 |
| 12 | 609.378 | Torvoside G TG(15:0/15:0/15:0) | HMDB0030337 |
| 13 | 645.602 | CE(16:1(9Z)) | HMDB0000658 |
| 14 | 693.347 | all-trans-Heptaprenyl diphosphate | HMDB0012187 |
| 15 | 720.528 | PC(15:0/16:0) | HMDB0007935 |

TABLE 1-continued

| | m/z | Name of potential substance | HMDB ID |
|---|---|---|---|
| 16 | 766.023 | NADP | HMDB0000217 |
| 17 | 973.878 | TG(20:0/20:0/20:1(11Z)) | HMDB0005415 |

The invention claimed is:

1. A composition serving as a biomarker panel for detecting tuberculosis, comprising detecting reagents and 17 serum metabolic, wherein the detecting reagents comprising an iron particle matrix, and the 17 serum metabolites consisting of D-Leucic acid, leucic acid, L-Cystine, MG (0:0/14:0/0:0), S-Lactoylglutathione, Octacosanoic acid, Cer (d18: 1/12:0), Raffinose, LysoPC (20:1(11Z)/0:0), LysoPC (22:4(7Z,10Z,13Z,16Z)/0:0), PC(18:1(9Z)e/2:0), Torvoside CE(16:1(9Z)), all-trans-Heptaprenyl diphosphate, PC (15:0/16:0), Nicotinamide Adenine Dinucleotide Phosphate (NADP), TG(20:0/20:0/20:1 (11Z)), the biomarker panel can be utilized for differential diagnosis of tuberculosis.

* * * * *